United States Patent [19]

Yamawaki et al.

[11] Patent Number: 4,696,929
[45] Date of Patent: Sep. 29, 1987

[54] DERIVATIVE OF PIPERAZINE HAVING ANTI-ALLERGIC AND ANTI-INFLAMMATORY ACTION

[75] Inventors: Ichiro Yamawaki; Kazuo Ogawa; Naohiko Ono; Takaji Honna; Sekio Nagayama, all of Tokushima; Mitsugi Yasumoto, Honjo, all of Japan

[73] Assignee: Taiho Pharmaceutical Company, Limited, Tokyo, Japan

[21] Appl. No.: 809,876

[22] Filed: Dec. 17, 1985

[30] Foreign Application Priority Data

Dec. 27, 1984 [JP] Japan .................. 59-276273

[51] Int. Cl.⁴ .................. A61K 31/495; C07D 403/12
[52] U.S. Cl. .................. 514/253; 544/373
[58] Field of Search .................. 544/373; 514/253

[56] References Cited

U.S. PATENT DOCUMENTS 3,316,260 4/1967 Shen et al. .................. 544/373
3,316,267 4/1967 Shen et al. .................. 544/373
3,985,878 10/1976 Makovec et al. .................. 514/255

FOREIGN PATENT DOCUMENTS 46-39875 11/1971 Japan .................. 544/373

OTHER PUBLICATIONS

Carron et al, Chem. Abst., 80-47862z.
Makovec et al, Chem. Abst., 84-180296s.
Taiho Pharm. Co. Ltd., Chem. Abst., 103-54100w.
Keck et al, Chem. Abst., 95-187045v.

*Primary Examiner*—Donald G. Daus
*Assistant Examiner*—Cecilia Shen
*Attorney, Agent, or Firm*—Murray and Whisenhunt

[57] ABSTRACT

A piperazine derivative represented by the formula (I) below

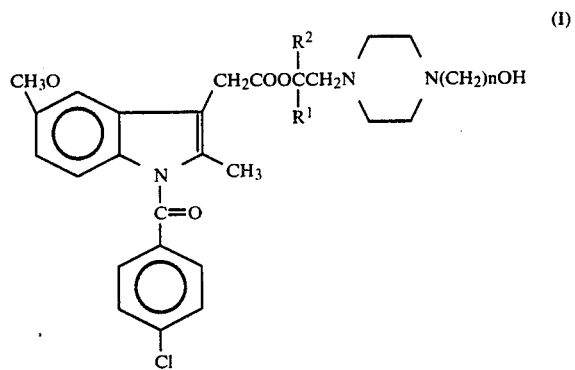

wherein $R^1$ is lower alkyl or phenyl, $R^2$ is hydrogen or lower alkyl, n is an integer of 2 to 10, is useful as an effective component of anti-inflammatory agent or anti-allergic agent.

4 Claims, No Drawings

DERIVATIVE OF PIPERAZINE HAVING ANTI-ALLERGIC AND ANTI-INFLAMMATORY ACTION

The invention relates to a novel piperazine derivative, an acid salt thereof, process and use thereof.

Indomethacin is widely used as an anti-inflammatory agent and is considered to exhibit the anti-inflammatory effect by restricting the production of prostaglandins and thromboxane by inhibiting the cyclooxygenase action. However, investigation has recently been made on cascade substances of arachidonic acid and their pharmacological action. As a result, it is found that leucotriene which is lipoxygenase metabolite of arachidonic acid is also an important mediator of inflammation and allergy. However, indomethacin is considered to have a limited anti-inflammatory effect since it has cyclooxygenase-inhibiting action but does not inhibit lipoxygenase reaction.

Although benoxaprofen [2-(4-chlorophenyl)-α-methyl-5-benzoxazoleacetic acid] is known as a sole example of drug having both of the aboe cyclooxygenase-inhibiting and lipoxygenase-inhibiting actions, the development of this drug was suspended. Accordingly, drugs of this kind are desired to be developed.

An object of the invention is to provide a novel piperazine derivative which has a lipoxygenase-inhibiting action and an excellent anti-inflammatory action.

Another object of the invention is to provide a process for preparing the above piperazine derivative.

Still another object of the invention is to provide an anti-inflammatory agent or antiallergic agent containing the above piperazine derivative.

The above and other objects of the invention will be apparent from the following description.

The invention provides a piperazine derivative represented by the formula (I) below.

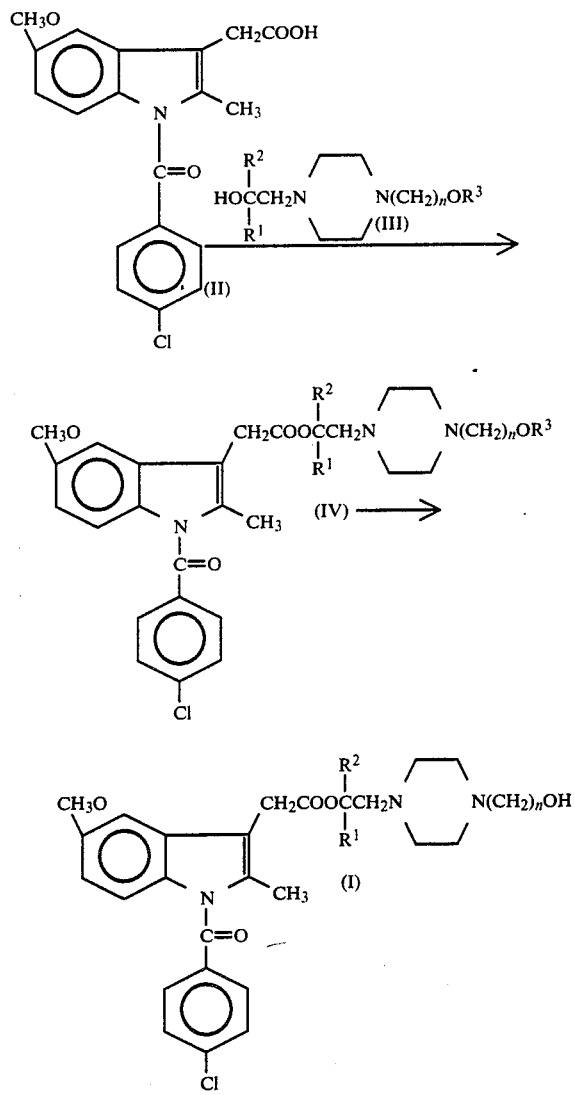

wherein $R^1$ is lower alkyl or phenyl, $R^2$ is hydrogen or lower alkyl, n is an integer of 2 to 10.

In the above formula (I), examples of lower alkyl groups in $R^1$ and $R^2$ are methyl, ethyl, propyl, butyl and like alkyl groups having 1 to 4 carbon atoms. Acid salts of the compound represented by the formula (I) include those usable as a pharmaceutical and are salts of hydrochloric acid, hydrobromic acid, sulfuric acid or like inorganic acids and of citric acid, maleic acid, lactic acid, oxalic acid, tartaric acid, or like organic acids.

The above piperazine derivative of the formula (I) and acid salt thereof in the invention have an anti-inflammatory action and lipoxygenase-inhibiting action and are useful as an anti-inflammatory agent or antiallergic agent.

In the following are explained methods of preparation of the piperazine derivative of the formula (I) of the invention.

The present piperazine derivative (I) can be prepared as shown in the equations below by subjecting indomethacin (II) and an alcohol derivative (III) which is protected in one hydroxyl group to a usual esterification reaction and subsequently eliminating the protecting group from the resulting compound of the formula (IV) by a known manner.

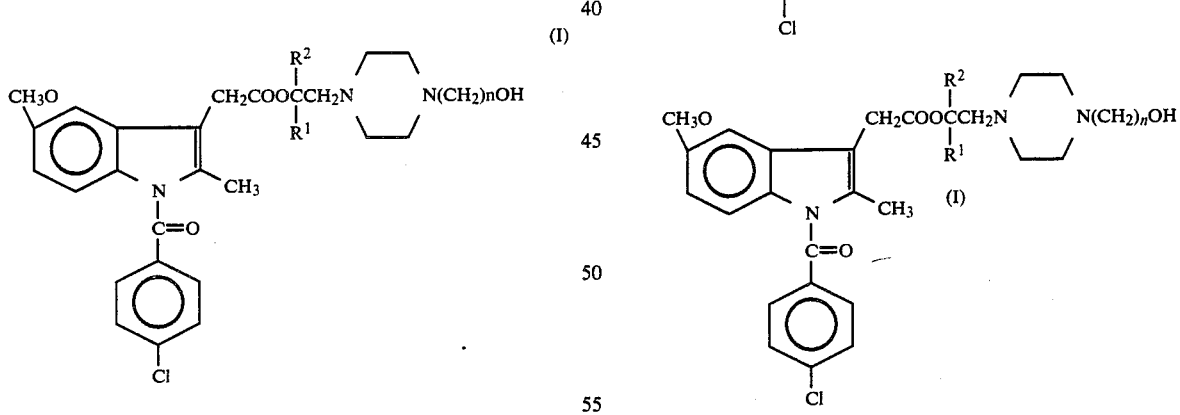

wherein $R^1$, $R^2$ and n are as defined above, $R^3$ is a protecting group of the alcohol.

In the above formula (III), the protecting groups of the alcohol in $R^3$ are any of known protecting groups and are for example tetrahydrofuranyl, tetrahydropyranyl, t-butyldimethylsilyl, etc.

In the above esterification reaction, the compound (II) which is activated in carboxyl group is usable in place of the compound (II) per se. The reaction using the activated starting material can also be conducted under the same reaction condition and operation as in the known esterification reaction. The reaction can easily be carried out in more detail by any of the following methods.

(a) Dicyclohexylcarbodiimide method;

Indomethacin (II) is reacted with dicyclohexylcarbodiimide and the alcohol derivative (III).

(b) Carboxylic acid halide method;

Acid halide of indomethacin (II) is reacted with the alcohol derivative (III).

(c) Carbonyldiimidazole method;

Indomethacin (II) is reacted with carbonyldimidazole and the resulting product is reacted with the alcohol derivative (III).

(d) Carboxylic acid anhydride method;

Indomethacin (II) is reacted with acetic anhydride or like dehydrating agent and the resulting carboxylic acid anhydride is reacted with the alcohol derivative (III).

Among the above methods (a) to (d), particularly preferable are dicyclohexylcarbodiimide method (a) and carboxylic acid halide method (b).

In dicyclohexylcarbodiimide method (a), the reaction is preferably conducted in the presence of a catalytic amount of 4-dimethylaminopyridine in a solvent at a temperature of $-20°$ to $100°$ C., preferably $-10°$ to $50°$ C. The alcohol derivative (III) can be used in an excess amount to indomethacin (II) but is preferably used in an amount of about 0.8 to 2 moles per mole of indomethacin. Excess of dicyclohexylcarbodiimide is usable to indomethacin (II) but is preferably used in about 1 to 4 times moles of the theoretical amount. The solvent is any of those inert to the reaction and is for example chloroform, dichloromethane and like halogenated hydrocarbons, acetonitrile, dimethylformamide (DMF) and like polar solvents, dioxane, tetrahydrofuran and like ethers, etc.

In the above reaction, the starting alcohol derivative (III) is prepared, for example, by reacting a compound (V) of the formula

 (V)

with a compound (VI) of the formula

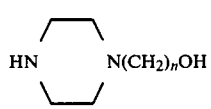 (VI)

in an appropriate solvent and with or without use of a basic compound at a temperature of $0°$ to $200°$ C. and protecting the hydroxyl group of the resulting compound (VII) of the formula

 (VII)

by a usual method to obtain a compound (VIII) of the formula

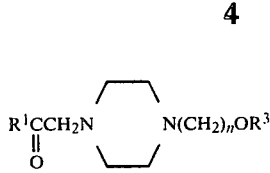 (VIII)

and reducing the compound (VIII) in an appropriate solvent. In the above, $R^1$, $R^3$ and n are as defined above and X is halogen.

The alcohol derivative (III) can also be prepared by reacting a compound (IX) of the formula

 (IX)

with a compound (X) of the formula

 (X)

in an appropriate solvent and with or without use of a basic compound at a temperature of $0°$ to $200°$ C. In the above, $R^1$, $R^2$, $R^3$, n and X are as defined above. The synthesis of the alcohol derivative (III) is described in detail in the later Reference Examples.

In case of carboxylic acid halide method using an acid halide of indomethacin, the reaction is preferably conducted in a solvent at a temperature of $-20°$ to $150°$ C., preferably $-10°$ to $100°$ C. The reaction is preferably carried out in the presence of a basic compound such as pyridine, piperazine, piperidine, morpholine, triethylamine, 1,8-diazabicyclo[5,4,0]-7-undecene, etc. As a solvent, usable are those mentioned in the above dicyclohexylcarbodiimide method. The starting alcohol derivative (III) is any of those prepared in the above methods. The alcohol derivative (III) can be used in an excess amount to the acid halide of indomethacin but is preferably used in an amount of about 0.5 to 2 times moles of the theoretical amount. The basic compound is usable in an excess amount to the acid halide of indomethacin but is preferably used in an amount of about 1 to 4 times moles of the theoretical amount.

The compound (IV) obtained by the method (a) or (b) can be isolated after the reaction by a usual method.

The desired compound (I) can be obtained by eliminating the protecting group of the compound (IV) by a known method. The present compound (I) obtained by the above reactions can be isolated by a usual method and is, when desired, converted to an appropriate acid salt by a usual method.

The present piperzine derivative is useful as an effective component of anti-inflammatory agent or antiallergic agent. These agents are formulated into any of known pharmacological forms when administered to a mammal including a man, such as oral preparation, injection, rectal suppository or inhalant, in accordance with the purpose of therapy contemplated. Such preparations can be formulated in the manner already known in the art, using conventional pharmacologically acceptable, non-toxic carriers or excipients. For the formulation of solid preparations for oral administration, such as tablets, coated tablets, granules, powders and capsules, excipients and, when required, binders, disintegrators, lubricants or glazes, coloring agents, corrigents, etc, can be added to the compound of this invention. Such additives are already known in the art and useful examples are excipients such as lactose, white sugar, sodium chloride, glucose solution, starch, calcium carbonate, kaolin, crystaline cellulose and silicic acid; binders such as water, ethanol, propanol, glucose, carboxymethylcellulose, shellac, methylcellulose, potassium phosphate and polyvinylpyrrolidone, disintegrators such as dried starch, sodium alginate, agar power, sodium hydrogencarbonate, calcium carbonate, sodium lauryl sulfate, glyceryl monostearate, starch and lactose; lubricants or glazes such as purified talc, stearic acid salt, boric acid powder, solid polyethylene glycol; corrigents such as sucrose, compound bitter orange peel, citric acid, tartaric acid, etc. For the formulation of liquid preparations for oral administration, such as solutions for oral administration, syrups, etc., conventional corrigents, buffers, stabilizers, etc, can be added to the present compound. Such preparations can be formulated in the usual manner. Examples of useful corrigents are those exemplified above. Typical buffers include sodium citrate. Stabilizers include tragacanth, gum arabic, gelatin, etc. The pharmacological compositions thus prepared are orally administered. Parenteral solutions can be formulated in the usual manner using distilled water for injection as the carrier and adding to the present compound conventional additives such as pH-adjusting agents, buffers, stabilizers, isotonic agents, local anesthetics, etc. Examples of the pH-adjusting agents and buffers are sodium salts of citric acid, acetic acid and phosphoric acid. The stabilizers include sodium pyrosulfite (anti-oxidant), EDTA, thioglycolic acid, thiolactic acid, etc. Examples of useful local anesthetics are procaine hydrochloride, xylocaine hydrochloride, lidocaine hydrochoride, etc. Such solutions can be given subcutaneously, intramascularly or intravenously. For the prepartion of rectal suppositories, conventional excipients such as fatty acid triglyceride and like base and if required, Tween and like surfactants, etc. can be added to the present compound, followed by formulation in the usual manner. Such suppositories are administered to the rectum. Inhalants can be prepared in the usual manner by adding to the present compound a conventional propellant such as flon gas, etc., and other conventional additives, if desired.

The amount of the present compound to be incorporated into the foregoing preparations varies with the symptoms of the patient or with the type of the preparation. Preferably the amount per administration unit is about 50 to about 500 mg for oral administration, about 10 to about 200 mg for parenteral administration, and about 50 to about 500 mg for intrarectal administration. The dosage per day for an adult, which is variable with the symptoms, age, and the like, is preferably about 30 to about 500 mg for usual purposes.

The invention will be described below in more detail with reference to Reference Examples in which the starting alcohol derivatives (III) are prepared and Examples in which the present compounds are prepared.

REFERENCE EXAMPLE 1

Preparation of 3-(4-phenacyl-1-piperazinyl)propanol

To a mixture of 50 ml of dichloromethane and 3.00 g of 3-(1-piperazinyl)propanol was added 4.20 g of phenacyl bromide. The mixture was stirred at room temperature over night. The reaction mixture was concentrated, dissolved into water and washed with ether. The equeous layer was adjusted to a pH of 11 with addition of an aqueous solution of sodium hydroxide and was extracted with dichloromethane. The dichloromethane layer was concentrated to obtain 5.18 g (yield 94.9%) of 3-(4-phenacyl-1-piperazinyl)propanol (Compound 1).

REFERENCE EXAMPLES 2 AND 3

Compounds 2 and 3 were prepared in the same manner as in Reference Example 1.

REFERENCE EXAMPLE 4

Preparation of 1-(t-butyldimethylsilyloxy)-3-(4-phenacyl-1-piperazinyl)propane

To a mixture of 80 ml of dichloromethane, 5.20 g of 3-(4-phenacyl-1-piperazinyl)propanol and 3.60 g of t-butyldimethylsilyl chloride was added dropwise 3.7 ml of triethylamine at room temperature. The mixture was stirred for 20 hours and then concentrated. The residue was purified by silica gel column chromatography (ethanol:chloroform=1:10) to obtain 7.16 g (yield 96.0%) of 1-(t-butyldimethylsilyloxy)-3-(4-phenacyl-1-piperazinyl)propane (Compound 4).

REFERENCE EXAMPLES 5 AND 6

Compounds 5 and 6 were prepared in the same manner as in Reference Example 4.

REFERENCE EXAMPLE 7

Preparation of 2-[4-{3-(t-butyldimethylsilyloxy)propyl}-1-piperazinyl]-1-phenylethanol To a mixture of 150 ml of methanol and 5.00 g of 1-(t-butyldimethylsilyloxy)-3-(4-phenacyl-1-piperazinyl)propane was added 0.85 g of sodium borohydride under ice-cooling condition. The mixture was stirred for 1 hour at room temperature, concentrated and extracted with dichloromethane. The dichloromethane layer was washed with water and then concentrated. The residue was purified by silica gel column chromatography (ethanol:chloroform=1:10) to obtain 4.50 g (yield 89.5%) of 2-[4-{3-(t-butyldimethylsilyloxy)propyl}-1-piperazinyl]-1-phenylethanol (Compound 7).

REFERENCE EXAMPLES 8 AND 9

Compounds 8 and 9 were prepared in the same manner as in Reference Example 7.

REFERENCE EXAMPLE 10

Preparation of 1-methyl-2-[4-{5-(2-tetrahydropyranyloxy)pentyl}-1-piperazinyl]ethanol To 20 ml of benzene were added 6.00 g of 1-methyl-2-(1-piperazinyl)ethanol and 8.60 g of 5-(2-tetrahydropyranyloxy)pentyl chloride and the mixture was refluxed for 24 hours. The reaction mixture was concentrated and the residue was purified by silica gel column chromatography (ethanol:chloroform=1:5) to obtain 11.6 g (yield 88.5%) of 1-methyl-2-[4-{5-(2-tetrahydropyranyloxy)pentyl}-1-piperazinyl]ethanol (Compound 10).

REFERENCE EXAMPLES 11 AND 12

Compounds 11 and 12 were prepared in the same manner as in Reference Example 10.

REFERENCE EXAMPLE 13

Preparation of 1,1-dimethyl-2-[4-{3-(2-tetrahydropyranyloxy)propyl}-1-piperazinyl]ethanol To 100 ml of benzene were added 9.61 g of 1-chloro-3-(2-tetrahydropyranyloxy)propane and 11.8 g of 2-(N-piperazino)methyl-2-hydroxypropane. The mixture was refluxed for 16 hours. The reaction mixture was cooled and washed with 100 ml of an aqueous solution of 2N—NaOH. The organic layer separated was dried with anhydrous $Na_2SO_4$ and the solvent was removed. The residue was purified by silica gel column chromatography (chloroform:methanol=5:1) to obtain 4.1 g (yield 25.3%) of 1,1-dimethyl-2-[4-{3-(2-tetrahydropyranyloxy)propyl}-1-piperazinyl]ethanol (Compound 13) in the form of oil.

Tables 1 and 2 show the properties of Compounds 1 to 13.

TABLE 1

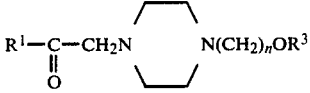

$$R^1-\underset{\underset{O}{\|}}{C}-CH_2N\diagup\diagdown N(CH_2)_nOR^3$$

| No. | $R^1$ | $R^3$ | n | NMR (CDCl₃, ppm) |
|---|---|---|---|---|
| 1 | phenyl | —H | 3 | 1.50~2.00(2H, —CH₂C$\underline{H}$₂CH₂OH), 2.50~2.75(10H, —N⟨ ⟩NC$\underline{H}$₂—), 3.50~3.75(4H, —COC$\underline{H}$₂—, —C$\underline{H}$₂OH), 4.78(1H, —OH), 7.35~8.00(5H, phenyl) |
| 2 | " | " | 2 | 2.2~2.6(10H, —N⟨ ⟩NC$\underline{H}$₂—), 2.48(2H, —C$\underline{H}$₂OH), 3.80(2H, phenyl-COC$\underline{H}$₂—), 7.3~7.7, 7.8~8.1 (5H, phenyl) |
| 3 | —CH₃ | " | 3 | 1.50~1.95(2H, —CH₂C$\underline{H}$₂CH₂OH), 2.12(3H, CH₃CO—), 2.15~2.75(10H, —N⟨ ⟩NC$\underline{H}$₂—), 3.12(2H, CH₃COC$\underline{H}$₂—), 3.70(2H, —C$\underline{H}$₂OH), 4.60(1H, OH) |
| 4 | phenyl | —SiC(CH₃)₃, (CH₃)₂ | 3 | 0.01[6H, Si(CH₃)₂], 0.82[9H, SiC(CH₃)₃], 1.50~2.00(2H, —CH₂C$\underline{H}$₂CH₂O—), 2.24~2.63(10H, —N⟨ ⟩NC$\underline{H}$₂—), 3.54(2H, —CH₂O—), 3.63(2H, —COCH₂—), 7.24~8.00(5H, phenyl) |
| 5 | " | " | 2 | 0.07[6H, Si(CH₃)₂], 0.89[9H, SiC(CH₃)₃], 2.2~2.7(10H, —N⟨ ⟩NC$\underline{H}$₂—), 3.70(2H, —CH₂O—), 3.70(2H, —COCH₂—), 7.4~7.7, 7.9~8.1(5H, phenyl) |
| 6 | —CH₃ | " | 3 | 0.01[6H, Si(CH₃)₂], 0.83[9H, SiC(CH₃)₃], 1.46~1.92(2H, —CH₂C$\underline{H}$₂CH₂O—), 2.07(3H, —COCH₃), 2.43(8H, —N⟨ ⟩N—), 2.23~2.56(2H, —C$\underline{H}$₂CH₂CH₂O—), |

TABLE 1-continued $$R^1-\underset{\underset{O}{\|}}{C}-CH_2N\overset{\frown}{\underset{\smile}{\phantom{XXX}}}N(CH_2)_nOR^3$$

| No. | $R^1$ | $R^3$ | n | NMR (CDCl$_3$, ppm) |
|---|---|---|---|---|
| | | | | 3.1(2H, —CH$_2$CO—), 3.56(2H, —CH$_2$O—) |

TABLE 2

$$HO\underset{\underset{R^1}{\|}}{\overset{\overset{R^2}{\|}}{C}}CH_2N\overset{\frown}{\underset{\smile}{\phantom{XXX}}}N(CH_2)_nOR^3$$

| No. | $R^1$ | $R^2$ | $R^3$ | n | NMR(CDCl$_3$, ppm) |
|---|---|---|---|---|---|
| 7 | —C$_6$H$_5$ | —H | —SiC(CH$_3$)$_3$(CH$_3$)$_2$ | 3 | 0.01[6H,Si(CH$_3$)$_2$], 0.85[9H,SiC(CH$_3$)$_3$], 1.50~1.85(2H,—CH$_2$CH$_2$C$\underline{H}_2$O—), 2.20~2.83(10H,—N⌒N—CH$_2$—), 3.56(2H,—CH$_2$O—), 3.80(1H,OH), 4.66,4.53(1H,—C$\underline{H}$—), 7.17(5H,C$_6$H$_5$) |
| 8 | " | —H | " | 2 | 0.03[6H,Si(CH$_3$)$_2$], 0.86[9H,SiC(CH$_3$)$_3$], 2.2~2.7(12H,—CH$_2$N⌒NCH$_2$—), 3.65(2H,—CH$_2$O—), 4.5~4.8(1H,—C$\underline{H}$—), 4.94(1H,OH), 7.0~7.4(5H,C$_6$H$_5$) |
| 9 | —CH$_3$ | —H | " | 3 | 0.01[6H,Si(CH$_3$)$_2$], 0.83[9H,SiC(CH$_3$)$_3$], 1.10(3H,HOCHC$\underline{H}_3$), 1.50~2.00(2H,—CH$_2$C$\underline{H}_2$CH$_2$O—), 2.15~2.85(12H,—CH$_2$N⌒NCH$_2$—), 3.50~4.00(3H,OH,—CH$_2$O—) |
| 10 | " | —H | 2-tetrahydropyranyl | 5 | 1.13(3H,—CHC$\underline{H}_3$), 1.2~2.0(12H,—CH$_2$(C$\underline{H}_2$)$_3$CH$_2$O—, tetrahydropyran H's), 2.1~2.9(12H,—CH$_2$N⌒NCH$_2$—), 3.0~4.1(5H,—C$\underline{H}$—,—CH$_2$O tetrahydropyranyl), 4.5~4.7(1H, tetrahydropyranyl) |
| 11 | " | —H | " | 6 | 1.13(3H,—CHC$\underline{H}_3$), 1.2~2.0(14H,—CH$_2$(C$\underline{H}_2$)$_4$CH$_2$O—, tetrahydropyran H's), 2.1~2.9(12H,—CH$_2$N⌒NCH$_2$—), 3.0~4.0(5H,—C$\underline{H}$—,—CH$_2$O tetrahydropyranyl), 4.5~4.7(1H, tetrahydropyranyl) |

TABLE 2-continued

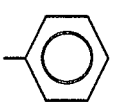

| No. | R¹ | R² | R³ | n | NMR(CDCl₃, ppm) |
|---|---|---|---|---|---|
| 12 | (phenyl) | —H | " | 10 | 1.0~2.0(22H, —CH₂(C$\underline{H}$₂)₈CH₂O—, (tetrahydropyran ring H)), 2.2~3.0(12H, —CH₂N<piperazine>NCH₂—), 3.2~4.1(4H, —C$\underline{H}$₂O<tetrahydropyran>H), 4.5~4.6(1H, <tetrahydropyran-H>), 4.5~4.8(1H, —C$\underline{H}$—), 7.1~7.4(5H, —phenyl) |
| 13 | —CH₃ | —CH₃ | " | 3 | 1.16(6H, —C(CH₃)₂C—), 1.40~2.00(8H, —CH₂CH₂CH₂—O— (tetrahydropyran H)), 2.30~2.80(12H, —CH₂N<piperazine>NCH₂—), 3.20~4.00(4H, —CH₂—O<tetrahydropyran-H>), 4.50~4.60(1H, <tetrahydropyran-H>) |

EXAMPLE 1

Preparation of 2-[4-{3-(t-butyldimethylsilyloxy)propyl}-1-piperazinyl]-1-phenylethyl 1-(p-chlorobenzoyl)-5-methoxy-2-methyl-3-indoylacetate A 0.74 ml-quantity of triethylamine was added to a mixture of 50 ml of dichloromethane, 1.80 g of 2-[4-{3-(t-butyldimethylsilyloxy)propyl}-1-piperazinyl]-1-phenylethanol and 2.00 g of acid chloride of indomethacin under ice-cooling condition. The mixture was stirred for 3 hours at the same temperature. The reaction mixture was washed with water and concentrated. The residue was purified by silica gel column chromatography (ethanol:chloroform=1:10) to obtain 3.14 g (yield 92.1%) of 2-[4-{3-(t-butyldimethylsilyloxy)-propyl}-1-piperazinyl]-1-phenylethyl 1-(p-chlorobenzoyl)-5-methoxy-2-methyl-3-indoylacetate.

NMR (CDCl₃, δ, ppm)

0.01 [6H, Si(CH₃)₂], 0.85 [9H, SiC(CH₃)₃], 1.50~1.83(2H, —CH₂C$\underline{H}$₂CH₂O—), 2.00~2.80(15H,

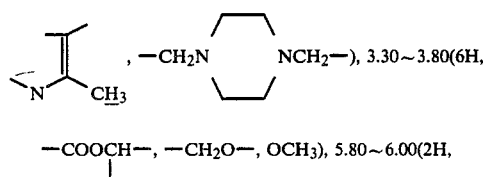, —CH₂N<piperazine>NCH₂—), 3.30~3.80(6H,

—COOC$\underline{H}$—, —CH₂O—, OCH₃), 5.80~6.00(2H,

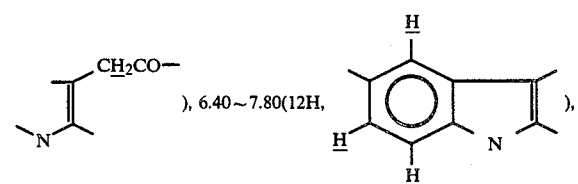), 6.40~7.80(12H, <indole-H>, 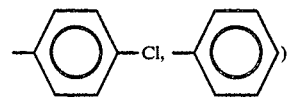)

EXAMPLE 2

Preparation of
2-[4-{3-(t-butyldimethylsilyloxy)propyl}-1-piperazinyl]-1-methylethyl
1-(p-chlorobenzoyl)-5-methoxy-2-methyl-3-indoylacetate In the same manner as in Example 1, 3.24 g (yield 86.9%) of 2-[4-{3-(t-butyldimethylsilyloxy)propyl}-1-piperazinyl]-1-methylethyl 1-(p-chlorobenzoyl)-5-methoxy-2-methyl-3-indoylacetate was obtained by use of 50 ml of dichloromethane, 1.80 g of 2-[4-{3-(t-butyldimethylsilyloxy)propyl}-1-piperazinyl]-1-methylethanol and 2.40 g of acid chloride of indomethacin.

NMR(CDCl$_3$, δ, ppm) 0.01[6H,Si(CH$_3$)$_2$], 0.83[9H,SiC(CH$_3$)$_3$], 1.00~1.85(5H, —CHCH$_2$—, —CH$_2$CH$_2$CH$_2$O—),
　　　　　　　　　|
　　　　　　　　CH$_3$ 2.00~2.65(15H, 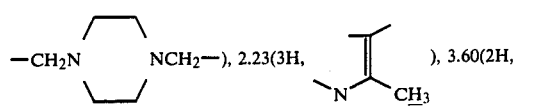, —CH$_2$N⟨⟩NCH$_2$—), 3.40~3.85(6H, —OCH$_3$, —CH—, —CH$_2$O—),
　　　　　　　　　　　　　　|

4.85~5.15(2H, 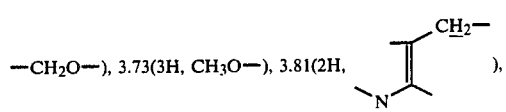), 6.35~7.65(7H, 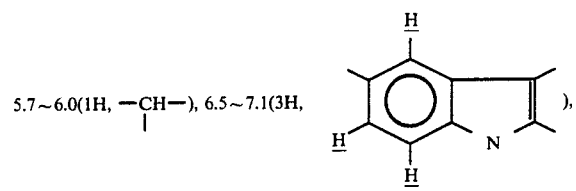)

EXAMPLE 3

Preparation of
2-[4-{2-(t-butyldimethylsilyloxy)ethyl}-1-piperazinyl]-1-phenylethyl
1-(p-chlorobenzoyl)-5-methoxy-2-methyl-3-indoylacetate A solution of 4.38 g of dicyclohexylcarbodiimide (DCC) in 20 ml of anhydrous dichloromethane was added dropwise to a mixture of 30 ml of anhydrous dichloromethane, 5.16 g of 2-[4-{2-(t-butyldimethylsilyloxy)ethyl}-1-piperazinyl]-1-phenylethanol, 5.06 g of indomethacin and a catalytic amount of 4-dimethylaminopyridine under ice-cooling condition. The mixture was stirred at room temperature over night. The reaction mixture was filtered and the filtrate was concentrated. The residue was purified by silica gel column chromatography (ethanol:chloroform = 1:20) to obtain 6.80 g (yield 81.7%) of 2-[4-{2-(t-butyldimethylsilyloxy)ethyl}-1-piperazinyl]-1-phenylethyl 1-(p-chlorobenzoyl)-5-methoxy-2-methyl-3-indoylacetate.

NMR (DMSO-d$_6$, δ, ppm)

0.01 [6H, Si(CH$_3$)$_2$], 0.84 [9H, SiC(CH$_3$)$_3$], 2.0~2.8(12H,

-continued
NMR (DMSO-d$_6$, δ, ppm)

—CH$_2$N⟨⟩NCH$_2$—), 2.23(3H, 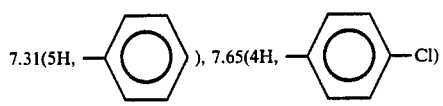), 3.60(2H,

—CH$_2$O—), 3.73(3H, CH$_3$O—), 3.81(2H, 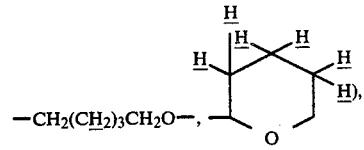), 5.7~6.0(1H, —CH—), 6.5~7.1(3H, 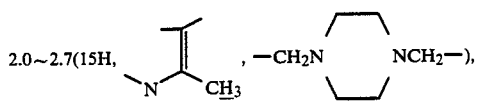),
　　　　　　　　　|

7.31(5H, —⟨⟩—), 7.65(4H, —⟨⟩—Cl)

EXAMPLE 4

Preparation of
1-methyl-2-[4-{5-(2-tetrahydropyranyloxy)pentyl}-1-piperazinyl]ethyl
1-(p-chlorobenzoyl)-5-methoxy-2-methyl-3-indoylacetate A solution of DCC (2.61 g) in 20 ml of anhydrous dichloromethane was added dropwise to a mixture of 30 ml of anhydrous dichloromethane, 2.65 g of 1-methyl-2-[4-{5-(2-tetrahydropyranyloxy)pentyl}-1-piperazinyl]ethanol, 3.02 g of indomethacin and a catalytic amount of 4-dimethylaminopyridine under ice-cooling condition. The reaction was conducted in the same manner as in Example 3 with use of the above mixture to obtain 4.80 g (yield 87.0%) of 2-methyl-2-[4-{5-(2-tetrahydropyranyloxy)pentyl}-1-piperazinyl]ethyl 1-(p-chlorobenzoyl)-5-methoxy-2-methyl-3-indoylacetate.

NMR(CDCl$_3$, δ, ppm) 1.21(3H, —CH—), 1.2~2.0(12H,
　　　　　　　　　　　　　　　　　　　　|
　　　　　　　　　　　　　　　　　　　CH$_3$ —CH$_2$(CH$_2$)$_3$CH$_2$O—, 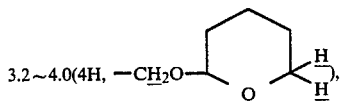), 2.0~2.7(15H, 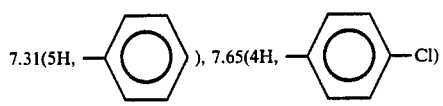, —CH$_2$N⟨⟩NCH$_2$—), 3.2~4.0(4H, —CH$_2$O—⟨⟩)

-continued 3.64(2H, 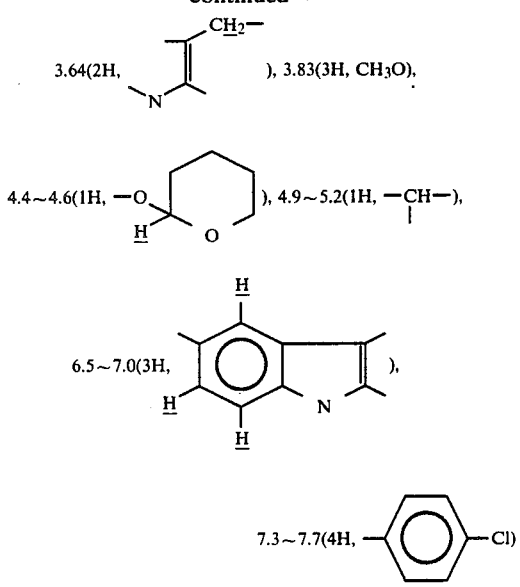), 3.83(3H, CH₃O), 4.4~4.6(1H, ), 4.9~5.2(1H, —CH—), 6.5~7.0(3H, ), 7.3~7.7(4H, ),

EXAMPLE 5

Preparation of
1-methyl-2-[4-{6-(2-tetrahydropyranyloxy)hexyl}-1-piperazinyl]ethyl
1-(p-chlorobenzyl)-5-methoxy-2-methyl-3-indoylacetate A solution of DCC (2.90 g) in 20 ml of anhydrous dichloromethane was added dropwise to a mixture of 30 ml of anhydrous dichloromethane, 3.08 g of 1-methyl-2-[4-{6-(2-tetrahydropyranyloxy)hexyl}-1-piperazinyl]ethanol, 3.35 g of indomethacin and a catalytic amount of 4-dimethylaminopyridine under ice-cooling condition. The reaction was conducted in the same manner as in Example 3 with use of the above mixture to obtain 4.80 g (yield 76.6%) of 1-methyl-2-[4-{6-(2-tetrahydropyranyloxy)hexyl}-1-piperazinyl]ethyl 1-(p-chlorbenzoyl)-5-methoxy-2-methyl-3-indoylacetate.

NMR (CDCl₃, δ, ppm)

1.21(3H, —CH—), 1.2~2.0(14H, —CH₂(CH₂)₄CH₂O—,
       |
       CH₃

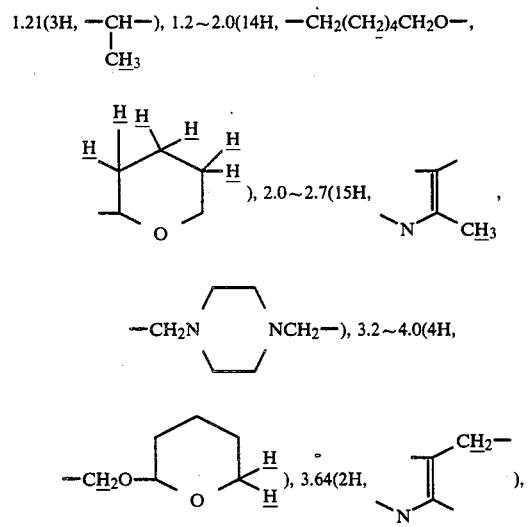), 2.0~2.7(15H, ,

—CH₂N  NCH₂—), 3.2~4.0(4H,

—CH₂O ), 3.64(2H, ),

-continued
NMR (CDCl₃, δ, ppm)

3.83(3H, CH₃O), 4.4~4.6(1H, ), 4.9~5.2(1H,

—CH—), 6.5~7.0(3H, ),
  |

7.3~7.7(4H, —Cl)

EXAMPLE 6

Preparation of
1-phenyl-2-[4-{10-(2-tetrahydropyranyloxy)decyl}-1-piperazinyl]ethyl
1-(p-chlorobenzoyl)-5-methoxy-2-methyl-3-indoylacetate A solution of DCC (2.61 g) in 20 ml of anhydrous dichloromethane was added dropwise to a mixture of 30 ml of dichloromethane, 4.47 g of 1-phenyl-2-[4-{10-(2-tetrahydropyranyloxy)decyl}-1-piperazinyl]ethanol, 3.58 g of indomethacin and a catalytic amount of 4-dimethylaminopyridine under ice-cooling condition. The reaction was conducted in the same manner as in Example 3 with use of the above mixture to obtain 6.60 g (yield 84.0%) of 1-phenyl-2-[4-{10-(2-tetrahydropyranyloxy)decyl}-1-piperazinyl]ethyl 1-(p-chlorobenzoyl)-5-methoxy-2-methyl-3-indoylacetate.

NMR(CDCl₃, δ, ppm) 1.0~2.0(22H, —CH₂(CH₂)₈CH₂O—,

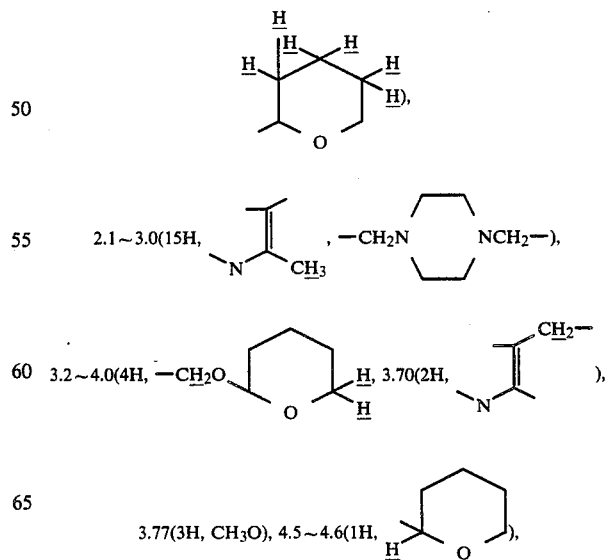), 2.1~3.0(15H, , —CH₂N  NCH₂—), 3.2~4.0(4H, —CH₂O ), 3.70(2H, ), 3.77(3H, CH₃O), 4.5~4.6(1H, ), -continued 5.8~6.0(1H, —CH—), 7.1~7.3(5H, 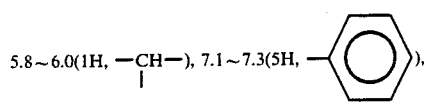), 6.5~7.0(3H, 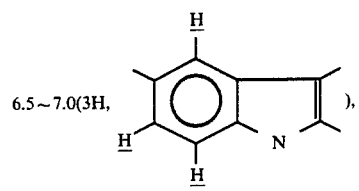), 7.3~7.7(4H, 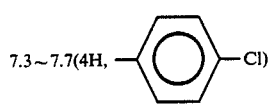—Cl)

EXAMPLE 7

Preparation of
2-{4-(3-hydroxypropyl)-1-piperazinyl}-1-phenylethyl
1-(p-chlorobenzyl)-5-methoxy-2-methyl-3-indoylacetate dimaleate A 1.80 g-quantity of 2-[4-{3-(t-butyldimethylsilyloxy)propyl}-1-piperazinyl]-1-phenylethyl 1-(p-chlorobenzoyl)-5-methoxy-2-methyl-3-indoylacetate obtained in Example 1 was dissolved into 50 ml of a mixture of acetic acid, tetrahydrofuran and water (30:1:1). The mixture was stirred for 24 hours at room temperature. The reaction mixture was concentrated and the residue was dissolved into water. The solution was adjusted to a pH of 8 to 9 with addition of sodium hydrogencarbonate and extracted with ethyl acetate. The ethyl acetate layer was dehydrated with addition of anhydrous sodium sulfate and then concentrated. The residue was dissolved into 53 ml of a mixture of ethanol and ethyl ether. Thereto was added a solution of 0.3 g of maleic acid in 10 ml of ethyl ether. Crystals separated from the solution and recrystallized from ethanol to obtain 1.84 g (yield 87.6%) of 2-{4-(3-hydroxypropyl)-1-piperazinyl}-1-phenylethyl 1-(p-clorobenzoyl)-5-methoxy-2-methyl-3-indoylacetate dimaleate.
mp 152°~153° C.

| Elementary analysis ($C_{42}H_{46}ClN_3O_{13} \cdot H_2O$) | | | |
|---|---|---|---|
| | C | H | N |
| Calculated (%) | 61.17 | 5.50 | 4.78 |
| Found (%) | 60.10 | 5.50 | 5.03 |

EXAMPLE 8

Preparation of
2-{4-(3-hydroxypropyl)-1-piperazinyl}-1-methylethyl
1-(p-chlorobenzoyl)-5-methoxy-2-methyl-3-indoylacetate dimaleate The reaction was conducted in the same manner as in Example 7 with use of 2.00 g of 2-[4-{3-(t-butyldimethylsilyloxy)propyl}-1-piperazinyl]-1-methylethyl 1-(p-chlorobenzoyl)-5-methoxy-2-methyl-3-indoylacetate obtained in Example 2 to prepare 1.98 g (yield 83.9%) of 2-{4-(3-hydroxypropyl)-1-piperazinyl}-1-methylethyl 1-(p-chlorobenzoyl)-5-methoxy-2-methyl-3-indoylacetate dimaleate.
mp 164°~166° C.

| Elementary analysis ($C_{37}H_{44}ClN_3O_{13}$) | | | |
|---|---|---|---|
| | C | H | N |
| Calculated (%) | 57.40 | 5.73 | 5.43 |
| Found (%) | 57.11 | 5.76 | 5.57 |

EXAMPLE 9

Preparation of
2-{4-(2-hydroxyethyl)-1-piperazinyl}-1-phenylethyl
1-(p-chlorobenzoyl)-5-methoxy-2-methyl-3-indoylacetate dimaleate The reaction was conducted in the same manner as in Example 7 with use of 5.00 g of 2-[4-{2-(t-butyldimethylsilyloxy)ethyl}-1-piperazinyl]-1-phenylethyl 1-(p-chlorobenzoyl)-5-methoxy-2-methyl-3-indoylacetate obtained in Example 3 to prepare 4.80 g (yield 82.2%) of 2-{4-(2-hydroxyethyl)-1-piperazinyl}-1-phenylethyl 1-(p-chlorobenzoyl)-5-methoxy-2-methyl-3-indoylacetate dimaleate.
mp 158°~159° C.

| Elementary analysis ($C_{41}H_{44}ClN_3O_{13}$) | | | |
|---|---|---|---|
| | C | H | N |
| Calculated (%) | 59.89 | 5.39 | 5.11 |
| Found (%) | 59.60 | 5.46 | 5.04 |

EXAMPLE 10

Preparation of
2-{4-(5-hydroxypentyl)-1-piperazinyl}-1-methylethyl
1-(p-chlorobenzoyl)-5-methoxy-2-methyl-3-indoylacetate dimaleate To 4.00 g of 1-methyl-2-[4-{5-(2-tetrahydropyranyloxy)pentyl}-1-piperazinyl]ethyl 1-(p-chlorobenzoyl)-5-methoxy-2-methyl-3-indoylacetate obtained in Example 4 were added 50 ml of methanol and 1.56 g of maleic acid. The mixture was refluxed for 3 hours and then allowed to cool to separate out crystals. Filtration of crystals gave 4.2 g (yield 85.6%) of 2-{4-(5-hydroxypentyl)-1-piperazinyl}-1-methylethyl 1-(p-chlorobenzoyl)-5-methoxy-2-methyl-3-indoylacetate dimaleate.
mp 168°~170° C.

| Elementary analysis ($C_{39}H_{48}ClN_3O_{13}$) | | | |
|---|---|---|---|
| | C | H | N |
| Calculated (%) | 58.39 | 6.03 | 5.24 |
| Found (%) | 58.12 | 5.95 | 5.21 |

EXAMPLE 11

Preparation of
2-{4-(6-hydroxyhexyl)-1-piperazinyl}-1-methylethyl
1-(p-chlorobenzoyl)-5-methoxy-2-methyl-3-indoylacetate dimaleate The reaction was conducted in the same manner as in Example 10 with use of 4.00 g of 1-methyl-2-[4-{6-(2-tetrahydropyranyloxy)hexyl}-1-piperazinyl]ethyl 1-(p-chlorobenzoyl)-5-methoxy-2-methyl-3-indoylacetate obtained in Example 5, 30 ml of methanol and 1.53 g of maleic acid to prepare 4.10 g (yield 83.8%) of 2-{4-(6-hydroxyhexyl)-1-piperazinyl}-1-methylethyl 1-(p- chlorobenzoyl)-5-methoxy-2-methyl-3-indoylacetate dimaleate.
mp 158°~159° C.

| Elementary analysis (C₄₀H₅₀ClN₃O₁₃) | | | |
|---|---|---|---|
|  | C | H | N |
| Calculated (%) | 58.86 | 6.17 | 5.15 |
| Found (%) | 58.73 | 6.23 | 5.10 |

EXAMPLE 12

Preparation of 2-{4-(10-hydroxydecyl)-1-piperazinyl}-1-phenylethyl 1-(p-chlorobenzoyl)-5-methoxy-2-methyl-3-indoylacetate dimaleate The reaction was conducted in the same manner as in Example 10 with use of 7.86 g of 1-phenyl-2-[4-{10-(2-tetrahydropyranyloxy)decyl}-1-piperazinyl]ethyl 1-(p-chlorobenzoyl)-5-methoxy-2-methyl-3-indoylacetate obtained in Example 6, 100 ml of methanol and 2.90 g of maleic acid to prepare 8.20 g (yield 87.8%) of 2-{4-(10-hydroxydecyl)-1-piperazinyl}-1-phenylethyl 1-(p-chlorobenzoyl)-5-methoxy-2-methyl-3-indoylacetate dimaleate.
mp 149°~151° C.

| Elementary analysis (C₄₉H₆₀ClN₃O₁₃) | | | |
|---|---|---|---|
|  | C | H | N |
| Calculated (%) | 62.98 | 6.47 | 4.50 |
| Found (%) | 62.77 | 6.61 | 4.36 |

EXAMPLE 13

Preparation of 1-methyl-2-[4-{3-(2-tetrahydropyranyloxy)propyl}-1-piperazinyl]-2-methyl-2-propyl 1-(p-chlorobenzoyl)-5-methoxy-2-methyl-3-indoylacetate Into 30 ml of dichloromethane were dissolved 2.9 g of 3-[4-(2-hydroxy-2-methylpropyl)-1-piperazinyl]-1-(2-tetrahydropyranyloxy)propane and 2.0 g of dimethylaminopyridine. To the solution was added dropwise a solution of 3.6 g of acid chloride of indomethacin in 20 ml of dichloromethane under a condition of ice-cooling. The mixture was stirred at room temperature overnight. The reaction mixture was washed with water, dried with anhydrous sodium sulfate and the solvent was removed. The residue was purified by silica gel column chromatography (chloroform:methanol=10:1) to obtain 2.43 g (yield 39.3%) of oily above desired compound.

NMR (CDCl₃, δ, ppm)

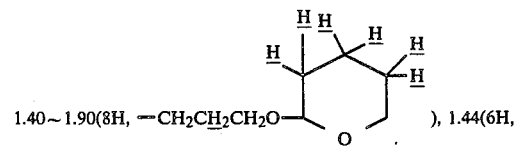
1.40~1.90(8H, —CH₂CH₂CH₂O—), 1.44(6H,

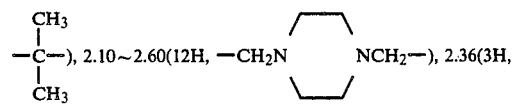
—C(CH₃)₂—), 2.10~2.60(12H, —CH₂N  NCH₂—), 2.36(3H,

NMR (CDCl₃, δ, ppm)

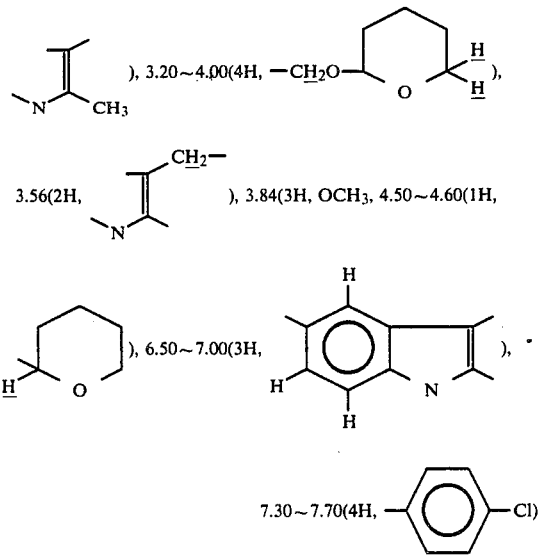

), 3.20~4.00(4H, —CH₂O—), 3.56(2H, ), 3.84(3H, OCH₃), 4.50~4.60(1H, ), 6.50~7.00(3H, ), 7.30~7.70(4H, —C₆H₄—Cl)

EXAMPLE 14

Preparation of 1-{(3-hydroxypropyl)-1-piperazinyl}-2-methyl-2-propyl 1-(p-chlorobenzoyl)-5-methoxy-2-methyl-3-indolyacetate dimaleate To 2.43 g of the compound of Example 13 were added 100 ml of methanol and 1.1 g of maleic acid. The mixture was refluxed for 2 hours and the solvent was removed. To the residue were added 20 ml of water, 50 ml of chloroform and 2 g of sodium hydrogencarbonate. The mixture was stirred for 20 minutes and then chloroform layer separated was concentrated. The resulting oily product was purified by silica gel column chromatography (chloroform:methanol=8:1). The oily product obtained was dissolved into 30 ml of ethyl ether. Thereto was added a solution of 0.88 g of maleic acid in 50 ml of ethyl ether under a condition of ice-cooling. The precipitate was filtered out and dried to obtain 2.2 g (yield 73.3%) of the above desired compound having a melting point of 140° to 142° C.

| Elementary analysis (C₃₈H₄₆ClN₃O₁₃) | | | |
|---|---|---|---|
|  | C | H | N |
| Calculated (%) | 57.90 | 5.88 | 5.33 |
| Found (%) | 58.10 | 5.73 | 5.30 |

Given below are examples of pharmacological compositions prepared by using the compounds of the present invention.

Preparation 1: Tablets

Tablets were prepared from the following composition (400 mg per tablet).

| | |
|---|---|
| Compound (Example 11) | 200 mg |
| Lactose | 47 mg |
| Corn starch | 50 mg |
| Crystalline cellulose | 50 mg |

| | |
|---|---|
| Hydroxypropyl cellulose | 15 mg |
| Talc | 2 mg |
| Magnesium stearate | 2 mg |
| Ethyl cellulose | 30 mg |
| Fatty acid glyceride | 2 mg |
| Titanium dioxide | 2 mg |
| Total: | 400 mg |

Preparation 2: Capsules

An encapsulated preparation was formulated from the following composition (250 mg per capsule).

| | |
|---|---|
| Compound (Example 9) | 100 mg |
| Lactose | 50 mg |
| Corn starch | 47 mg |
| Crystalline cellulose | 50 mg |
| Talc | 2 mg |
| Magnesium stearate | 1 mg |
| Total: | 250 mg |

Assay of 5-lipoxygenase

Preparation of PMNL (polymorphonuclear leukocyte)

Male Hartley strain guinea pigs weighing 580~740 g received intraperitoneal injection of 2% casein in saline (5 ml/100 g body weight). After 16~18 hr, the guinea pigs were sacrificed by bleeding from the carotid artery. Then 50 ml of Dulbecco's phosphate-buffered saline (PBS(−)) containing 5 units/ml of heparin were injected into the peritoneal cavity and peritoneal exudate was collected. The exudate was combined and filtered through 4 layers of cheese cloth, followed by centrifugation at 1,000 rpm for 10 min. Cell pellets were suspended in small amounts of PBS(−) and treated 3 volumes of 0.2% NaCl to lyse contamination red blood cells. The cells (80% or more PMNL as identified by Wright-Giemsa stain) were washed twice with buffer A (130 mM NaCl, 25 mM phosphate, pH 7.4, 1 mM EDTA). The washed cells ($1 \times 10^8$ cells/ml) were resuspended in 50 mM phosphate (pH 7.4) containing 1 mM EDTA and 0.1% gelatin, sonicated and centrifuged at $10,000 \times g$ for 20 min. The supernatant solution was further centrifuged at $105,000 \times g$ for 60 min to obtain the cytosol fraction.

Enzyme assays

Test compounds were dissolved in dimethyl sulfoxide (DMSO), and the final concentration of DMSO was kept at 1% in each experiment. The cytosol fraction (500 μl) was pre-incubated with test compounds in the presence of 1 mM $CaCl_2$ and 1 mM GSH (reduced glutathione) at 37° C. for 3 min, and the mixture was further incubated with [1−$^{14}$C]arachidonic acid (0.1 μCi) at 37° C. for 5 min. Each reaction was terminated by precipitating the proteins with 1 ml acetone and added 0.5 ml ice-cold saline. The pH was adjusted to about 3 with 150 μl 2N formic acid. The mixture was extracted twice with 2 ml chloroform. The organic layer was evaporated under a $N_2$ gas stream, redissolved in 30 μl of chloroform/methanol (2:1, v/v), and applied 20 μl to Silica gel TLC plates, and developed in the solvent system of petroleum ether/diethyl ether/acetic acid (50:50:1, v/v) for the separation of 5-lipoxygenase products. Radioactive zone of 5-HETE [5(S)-hydroxy-6,8,11,14-eicosatetraenoic acid] was detected by autoradiography, scraped from the TLC plates, and counted by a liquid scintillation counter. $IC_{50}$ (50% Inhibition Concentration) value indicates the concentration to decrease the enzymatic product by 50% as compared to that of vehicle-treated control.

| Compounds | $IC_{50}$ for 5-lipoxygenase ($\times 10^{-6}$ M) |
|---|---|
| Example 7 | 1.6 |
| Example 8 | 6.9 |
| Example 9 | 1.7 |
| Example 10 | 6.2 |
| Example 11 | 4.7 |
| Example 12 | 0.9 |
| Example 13 | 4.7 |
| Indomethacin | 242.4 |
| Benoxaprofen | 24.0 |

Assay of platelet cyclooxygenase

Preparation of washed platelet

Citrated blood (blood/3.8% sodium citrate=9:1 by volume) was obtained by heart-puncture from male New Zealand White rabbits weighing 3.21~4.75 kg and centrifuged at 1,000 rpm for 10 min. The platelet-rich plasma (the supernatant layer: PRP) was further centrifuged at 3,000 rpm for 10 min, and the resulting platelet was washed twice with buffer A (130 mM NaCl, 25 mM phosphate, pH 7.4, 1 mM EDTA). The washed platelets were resuspended in 50 mM phosphate (pH 7.4) containing 1 mM EDTA and adjusted $1 \times 10^8$ platelets/ml.

Enzyme assays

For the platelet cyclooxygenase assays, 1 ml of intact washed platelet suspensions were pre-incubated with test compounds (dissolved in DMSO) in the presence of 1 mM GSH at 37° C. for 3 min, and then the mixture was incubated with [1−$^{14}$C]arachidonic acid (0.1 μCi) at 37° C. for 5 min. Each reaction was terminated and extracted by the addition of 3 ml of ethyl acetate/methanol/1M citric acid (30:4:1, v/v). The organic layer was evaporated under a $N_2$ gas stream, redissolved in 30 μl of chloroform/methanol (2:1, v/v), and applied 20 μl to Silica gel TLC plates, and developed in the solvent system chloroform/methanol/acetic acid/$H_2O$ (90:8:1:0.8, v/v). Radioactive zone of $TXB_2$ (Thromboxane $B_2$) was detected by autoradiography, scraped from the TLC plates, and counted by a liquid scintillation counter. $IC_{50}$ value indicates the concentration to decrease the enzymatic product by 50% as compared to that of vehicle-treated control.

| Compounds | $IC_{50}$ for 5-HETE ($\times 10^{-6}$ M) |
|---|---|
| Example 7 | 20.4 |
| Example 8 | 30.6 |
| Example 9 | 9.2 |
| Example 10 | 22.8 |
| Example 11 | 41.2 |
| Example 13 | 22.3 |

What is claimed is:

1. A compound of the formula (I)

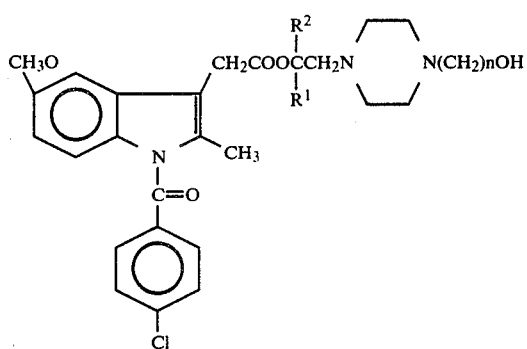

(I)

wherein $R^1$ is lower alkyl or phenyl, $R^2$ is hydrogen or lower alkyl, and n is an integer of 2 to 10, together with the pharmaceutically acceptable acid salts thereof.

2. A composition suitable for use as an anti-inflammatory agent, said composition comprising an effective amount of a compound as claimed in claim 1 or a pharmaceutically acceptable acid salt thereof, and a pharmaceutically acceptable carrier or excipient.

3. A method of treating an inflammatory condition in a patient in need of such treatment, said method comprising administering to said patient an anti-inflammatory effective amount of a compound of claim 1 or a pharmaceutically acceptable acid salt thereof.

4. A method of treating an allergic condition in a patient in need of such treatment, said method comprising administering to said patient an anti-allergic effective amount of a compound of claim 1, or a pharmaceutically acceptable acid salt thereof.

* * * * *